United States Patent [19]

Hellgren et al.

[11] Patent Number: 4,801,451
[45] Date of Patent: Jan. 31, 1989

[54] CLEANING WITH ENZYMES FROM KRILL

[76] Inventors: Lars G. I. Hellgren, Bronsgjutargatan 13, S-421 63 V:a Frölunda, Sweden; Viggo Mohr, St. Jørgensveita 6a, N-7000 Trondheim, Norway; Jan G. Vincent, Linnégatan 31, S-114 47 Stockholm, Sweden

[21] Appl. No.: 82,134

[22] Filed: Aug. 6, 1987

Related U.S. Application Data

[63] Continuation of Ser. No. 621,911, Jun. 18, 1984, abandoned.

[51] Int. Cl.[4] .................. A61K 37/54; A61K 37/62; C12N 9/64; D06M 16/00
[52] U.S. Cl. .................. 424/94.63; 252/DIG. 12; 424/94.6; 435/226; 435/264; 435/267; 435/268
[58] Field of Search ............... 435/174, 177, 226, 263, 435/264, 267, 268; 252/DIG. 12; 424/94.6, 94.63

[56] References Cited

U.S. PATENT DOCUMENTS 4,307,081 12/1981 Klein et al. .................. 424/94

FOREIGN PATENT DOCUMENTS 1273545 5/1972 United Kingdom ....... 252/DIG. 12

OTHER PUBLICATIONS

Chen et al., J. of Food Biochemistry, vol. 2, 1978, pp. 349–366.

*Primary Examiner*—David M. Naff
*Attorney, Agent, or Firm*—Bacon & Thomas

[57] ABSTRACT

Enzymes from animals belonging to the order Euphausiaaceae are used for cleaning. Preferably, an enzyme mixture containing exo-and endopeptidases from krill are used. Living tissue can be cleaned or debrided with the enzyme mixture, isolation of the enzymes may be carried out by homogenizing krill and extracting with an aqueous medium. Further purification can be by gel chromatography. Enzymes from which lipids have been extracted may be lyophilized for long time storage.

6 Claims, No Drawings

CLEANING WITH ENZYMES FROM KRILL

This application is a continuation of application Ser. No. 621,911, filed June 18, 1984, now abandoned.

FIELD OF THE INVENTION

This invention relates to a composition which contains a digestive and/or tissue enzyme preparation from an aquatic animal selected from the group consisting of animals belonging to the order Euphausiaceae or to the fishes. The composition is used in order to clean living or dead material by degrading and removing therefrom contaminants of biological origin or degradation products of such contaminants. The invention also provides a method for removing said contaminants from said material and a method for the preparation of a composition to be used according to the invention.

As used in the specification and in the claims, the term enzyme means an active enzyme if not otherwise specified.

The invention relates to both the therapeutical cleaning of mammals and to the non-therapeutical cleaning in general. The concept cleaning is hence used in its broadest meaning, i.e. cleaning of dead as well as of living material such as different types of textiles, hair, furs, skins, plastics, leather, nails, ears, mirrors, glass, porcelain, denture prosthesis, metals, stones, teeth, facades, downs, works of art such as paintings, etc. Cleaning also includes cleaning of humans and animals by removing substances such as pus (purulent exudate), fibrin, coagulated blood, blood crusts and necrotic tissue. This latter type of cleaning is especially important for the treatment of wounds, burns and dermatoses, e.g. for the so called enzymatic debridement, but can also be carried out in other areas of the living body, where the contaminants can occur. The uretra and the urinary bladder are examples of such other areas.

The normal digestive effect of the enzymes in the animals, as well as their autolytic action in the animals post mortem, are not included in the term cleaning.

TECHNICAL BACKGROUND

In krill (which belongs to the order Euphausiaceae), a mixture of different enzymes exists, such as e.g. proteinases (with acidic and neutral-to-alkaline pH-optimum), peptidases (exo- and endopeptidases), lipases, phospholipases, amylases and other carbohydrate degrading enzymes, phosphatases, nucleases, nucleotidases and esterases (T. E. Ellingsen; Biokjemiske Studier over Antarktisk Krill; Dr. ing avhandling; Institutt for Teknisk Biokjemi, Norges Tekniske Högskole, Trondheim (1982). The proteolytic (trypsin-like) activity existing in a water extract from krill has been studied and described (C.-S. Chen et al; J. Food Biochem. 2 (1978) p. 349-66)). Different protease activities in water extracts from capelin have also been described previously (A Gildberg; Autolysis of fish tissue—General aspects; Thesis; Institute of Fisheries; University of Tromsø Norway (1982)).

As early as 1913 proposals were made to use enzymes in detergents. Enzyme compositions for cleaning of dead materials, e.g. as laundry agents, have previously been based on different microbial proteases from the genus Bacillus. One such protease commonly used is subtilisin derived from *Bacillus subtilis* strains and marketed among others under the name Alcalase ® (Novo Industri, Copenhagen, Denmark). Different lipases have also been used for cleaning, especially for enabling degradation of lipids. In addition to enzymes, such compositions have contained also different anionic, cationic and neutral detergents together with blanchophores, such as perborates. The enzymes used hitherto have, like enzymes in general, been relatively unstable.

The most important enzyme compositions on the market for debridement of the components mentioned above are Streptokinase-streptodornase (Varidase ®, Lederle Lab., American Cyanamid Company, Wayne, N.J., USA), stabilized crystalline trypsin (Trypure ®, Novo Industri, Copenhagen, Denmark) and bovine fibrinolysin combined with deoxyribonuclease (Elase ®, Parke Davis & Company, Detroit, Mich., USA). Streptokinase acts on necrotic material mainly by its effect on DNA and streptodornase has a specific fibrinolytic effect. Trypsin acts proteolytically and is extracted from bovine pancreas. Fibrinolysin-deoxyribonuclease in a combination of two enzymes—one fibrin degrading enzyme and one acting on deoxyribonucleic acid which is an important component in pus.

One specific pepsin-like enzyme (pepsin I) from Mallotus villosus (capelin) has been proposed to be used in the medical treatment of burns (Gildberg A; cited above p. 89-90). The use of one specific enzyme acting on one type of substrates is likely to achieve only a limited breakdown of the contaminants present in wounds. However, no combination of this pepsinlike enzyme with other enzymes has been proposed for the therapeutical cleaning of humans.

The enzyme preparations mentioned above suffer from several drawbacks. Thus, all of them are relatively unstable leading to a rapid decrease in their activity, either during storage or use. Their activities are often limited to a certain pH-range, e.g. neutral to moderately alkaline pH. Their activities are also in many cases restricted to certain temperature intervals. At a temperature above +50° C., a rapid loss of activity is observed and at room temperatures or normal outdoor temperatures, their activities are low.

The effect of Varidase ®, Trypure ® and Elase ® are relatively poor for its purpose. Only a moderate debriding effect is usually achieved after a treatment over a period of three weeks.

THE OBJECTS OF THE INVENTION

One object of the present invention is to provide an improved cleaning composition with respect to the drawbacks mentioned above. Another object is to provide a method for the preparation of an improved composition to be used for the removal of contaminants containing substances of biological origin or degradation products from such substances, especially contaminants containing both proteins and lipids. A third object is to provide a new and improved method for cleaning living or dead material from the contaminants mentioned above, especially for the debridement of fibrin, coagulated blood and devitalized tissue by degrading these constituents and thereby facilitating their removal without apparently increasing their water content. The invention hence is based on compositions having more effective enzymes than the prior art compositions. This is valid for the total enzymatic effect on the contaminant in question.

THE INVENTION

These objects are achieved by using a composition containing an effective amount of an enzyme preparation which is capable of dissolving contaminants of biological origin and which derives from the animals mentioned in the introductory part. Enzyme mixtures from these animals can be obtained in a high yield and in a simple way. At present the most preferred and useful sources for the enzyme preparation are animals of the order Euphausiaceae, e.g. antarctic krill (*Euphausia superba*), *Euphausia crystallorophias*, and related species and other species of krill including *Meganyctiphanes norvegica, Tysanoessa inermis* and other related species. Among fishes, those of the genus Mallotus, particularly of the species *Mallotus villosus* (capelin), are preferred according to the invention. Among other sources, mackerel may be mentioned.

The most important enzyme activities for the invention appear to originate from the digestive tract of the animals. The complex mixture of different enzyme activities obtained from the animals is probably the explanation why the composition effects a surprisingly rapid degradation of biological contaminants irrespective of their origin. The enzymes are active in alkaline, neutral and acid medium, and can be utilized in cleaning compositions together with different surfactants (tensides and emulgators), and/or other components such as carriers and additives.

The fact that the composition may contain a mixture of enzymes makes it useful for the removal of contaminants containing mixtures of substances selected from the group consisting of lipids, phospholipids, biopolymers such as proteins, peptides, nucleic acids, mucopolysaccharides and polysaccharides, and degradation products of such compounds. These compounds are present in pus, blood crust and necrotic tissues.

According to the invention, particularly good results are obtained if the enzymes used have molecular weights within the range of 15 000 to 80 000 Daltons or active aggregates of such enzymes. Especially, enzymes having molecular weight from about 20 000 to about 40 000 Daltons are preferred. These ranges apply to enzymes obtained by a water extraction of the homogenized animals, i.e. especially to enzymes being water soluble during the extraction.

One embodiment of the invention relates to a new enzyme cleaning composition and to a method for the preparation thereof. The method is characterized in that an enzyme preparation, originating from an animal of the order Euphausiaceae or from a fish, is mixed with, dissolved in, bound to or otherwise combined with one or more water-insoluble or water-soluble aqueous or non-aqeuous carriers, if necessary together with suitable additives. The new composition may be in the form of an ointment, a powder, a paste, a cream, a spray, a gel, a liniment, a bandage, an oil, a tablet, a syrup, a granulate, a capsule, a tablet etc.

Certain non-sterile homogenous water solutions only consisting of buffer substances, water as the single solvent, and an enzyme preparation from the animals in question are excluded from the concept of the new composition. Such water solutions have been described in the publications cited above. The sample applies to lyophilized water extract containing no additives.

In the presently most preferred embodiment, the enzymes in the preparation used are water-soluble and-/or have molecular weights in the ranges mentioned above.

The invention also relates to a method for removing biological contaminants from living or dead material, e.g. by an enzymatic debridement. The method is characterized in that such contaminants being present on said material are contacted with an enzyme composition containing an effective amount of enzymes, e.g. a proteolytically and/or lipolytically effective amount of enzymes, originating from the animals mentioned above, whereafter the composition is removed from said material together with degraded or dissolved contaminants. In the presently most preferred embodiment, the method utilizes enzymes (including their active aggregates) having molecular weights from about 15 000 to about 80 000 Daltons or active aggregates of such enzymes. Especially, enzymes of molecular weights from about 20 000 to about 40 000 Daltons are preferred. Very great advantages are obtained for the removal of devitalized substances such as pus, blood crusts and necrotic tissue, and fibrin or coagulated blood. This is especially valid when these substances are removed from a living tissue.

The time period required to degrade and/or dissolve the contaminants varies from case to case, but should be selected sufficiently long to allow the enzymes to degrade and/or dissolve the contaminants. The treatment can be repeated, if necessary.

The enzyme preparation used may contain a wide variety of different enzymes e.g. of the types mentioned above. According to the invention it is possible to use compositions in which one or more of these enzymes have been removed by methods known per se, e.g. by adding an inhibitor specific for one enzyme or by removing the enzyme in question.

The proteolytic activity at optimum temperature is high in the pH-range 5–10. The pH-optimum is in the range 7–9. The temperature range for good proteolytic activity is 25°–70° C. and the optimal temperature is within the range of 30°–55° C. Activity is maintained down to 0° C.

The temperature and pH-ranges given above may all be utilized for different applications of the invention, although certain potential embodiments may also utilize other ranges.

The preparation of the enzymes from the animals is performed by well known methods. Hence, fresh or freshly frozen animals may be homogenized and extracted with aqueous medium (e.g. water). The extract obtained may be lyophilized and stored. The extract can be further purified e.g. by extraction with a lipid dissolving solvent in order to extract lipids. If further purification is required, gel-, ultra- or membrane filtration may be carried out. Other purification steps, which are potentially useful, are ion exchange and affinity chromatography. The extraction and the homogenization should be carried out in the cold below or close to +5° C.

The enzyme preparations which are obtained by a water extraction, may be used directly or, if necessary, after further purification. In most cases, it is of advantage to lyophilize a preparation from which lipids have been extracted. In such cases, the powder obtained may be stored for a long time. Each field of use requires specific compositions or forms thereof. Such forms are known per se. Thus the invention relates to enzyme compositions of different physical forms, such as lyophilized enzymes, homogeneous aqueous solutions or the enzyme compositions mentioned above and claimed to be new. The exact amount of enzymes in each composition varies from case to case—from the pure lyophilized extract to very complex detergent compositions. The amount of enzyme should be effective in degrading and/or dissolving the contaminants intended, without giving unnecessary adverse effects on the material from which the contaminants are to be removed. The other components in the new cleaning composition should be selected so that they will not adversely affect it under the condition required for its use.

The amount of the enzyme preparation existing in the final composition may vary from 0.0001% (w/w) up to 100%. With respect to protease activity, the final composition may contain from 0.0001 to 0.1 enzyme units per mg. Depending on the purity of the enzyme preparation used, other ranges may apply. The enzyme units above are given as μmol tyrosine equivalents per min with casein as substrate.

In compositions according to the invention different additives and carriers may be incorporated. Suitable carriers may be sterile, aqueous and physiologically acceptable salt solutions, organic and inorganic gel-forming materials, e.g. polymeric ones, silicone oils and other substances and mixtures thereof providing the desired physical properties of the composition. Among additives antimicrobials, perfumes, diffeent anionic, cationic, zwitterionic and neutral surfactants (tensides and emulgators) may be mentioned. Such components are already known per se in connection with other enzyme compositions for laundring or enzymatic debridement, see e.g. German patent application No. 2 130 833, GB patent specifications Nos. 1 280 497, 1 296 901 and 1 573 964 and U.S. Pat. Nos. 3 627 688, 3 855 142, 4 212 761, 4 243 546, 4 242 219, 4 287 082, 4 035 837 and 4 307 081, which all are incorporated herein by reference.

For treatment of injured living tissues, it is advantageous to use a composition containing a physiologically and pharmaceutically acceptable carrier or no carrier at all. Such a composition may be sterile. Sterilization may be carried out e.g. by sterile filtration when the composition is a solution. Sterile compositions may also be obtained by mixing sterile components under aseptic conditions.

The different embodiments of the invention will further appear from the claims, hereby enclosed to the specification. Below, the invention will be illustrated by different non-limiting examples.

EXAMPLE 1

A. Preparation of a krill extract

Krill, *Euphausia superba*, caught during the Antarctic summer and frozen immediately and stored for about 2 years at about −80° C., are placed in a room at about +5° C. When the krill is nearly thawed, 25 g of the krill is mixed with 50 ml of deionized water having a temperature of 0° C. The mixture is homogenized and then centrifuged in the cold (about 0° C.) for half an hour at 12 500 g. The red supernatant is decanted and saved. The sediment is resupended in 50 ml deionized water and centrifuged as above. The new supernatant is decanted and combined with the supernatant from the first extraction.

In order to remove lipids from the extract 20 ml of $CCl_4$ is added to the combined supernatant and homogenized in the cold (0° C.). The mixture is centrifuged at 2500 g for 15 min in the cold. The water-phase is removed and extracted once more with $CCl_4$ and centrifuged as described above. The waer-phase is used according to 1B, where it is referred to as the water extract.

B. Further purification by gel chromtography 20 ml of the water extract from A is chromtographed on Sephadex ® G-100 (dextran crosslinked with epichlorohydrin, Pharmacia Fine Chemicals AB, Uppsala, Sweden) in a column having a diameter of 3,1 cm and a height of 69 cm. The column is equillibrated and eluted (30 ml per hour) with Tris-HCl buffer (0.05M, pH 7.5) at +5° C. Fractions are collected. The elution profile is monitored spectrophotometrically by measuring the UV adsopriton at 280 nm and the proteolytic activity of the fractions are determined separately. The enzymatically active fractions are pooled and dialyzed against deionized water. Finally, the pooled fractions are lyophilized and used according to the invention.

The proteolytic activity in the fractions and in the lyophilized preparation is determined by using hemoglobin and/or casein as substrates (Rick, W I; Methods of Enzymatic analysis; Ed Bergmeyer, H U; Vol 2, p. 1013–23 (1974); Academic Press, New York). By carrying out gel chromatography, enzyme activity is mainly recovered from fractions corresponding to the molecular weights of 20 000 to 40 000 Daltons.

EXAMPLE 2

Preparation of a capelin extract

Capelin (*Mallotus villosus*), caught off the coast of Finnmark (Norway) in the month of September, was frozen and stored at −20° C. for one year. The frozen capelin was then placed at 5° C. After 24 hours the intestines including the digestive tract were removed from the partially thawed capelin. 25 g of intestines were mixed with 50 ml of deionized water and homogenized at 0° C. The mixture was subsequently centrifuged at 12500 g for half an hour. The partially cloudy supernatant is decanted and saved. The sediment is resuspended in 50 ml deionized water and centrifuged as above. The new supernatant is decanted and combined with the supernatant from the first extraction.

In order to remove lipids from the extract 20 ml of $CCl_4$ were added to the combined supernatant and homogenized in the cold (0° C.). The mixture was centrifuged at 2500 g for 15 min in the cold. The water-phase was removed and extracted once more with carbontetrachloride and centrifuged as described above. The water-phase was finally lyophilized.

EXAMPLE 3

Compositions containing enzymes from *Mallotus villosus*

A. 10 mg of a lyophilized enzyme preparation from capelin (according to example 2) are mixed with 0,4 mg calcium acetate and amylum resorb ad 1 g (Biosorb ®; Arbrook, Kirkton Campus, Livingston, Scotland).

The homogenous powder so obtained is agitated in 10 g of physiological sodium chloride solution (saline) and can be used for wet dressings.

B. 10 mg of the lyophilized capelin preparation (from example 2) are mixed with a polyethylene glycol gel (containing equal parts of Macrogol 600 and Macrogol 800 (Hoechst, Federal Republic of Germany)) ad 1 g. A 1% enzyme composition having a semi solid, homogenous consistency is obtained.

EXAMPLE 4

Composition containing krill enzymes in a solution 10 mg of a lyophilized enzyme preparation (from example 1B) are mixed with 0.4 mg calcium acetate and amylum resorb ad 1 g. The homogenous powder so obtained is shaken with 10 g saline and the composition obtained is used in order to soak a sterile compress having the size of 3×3 cm and containing 4 layers of a gauze. The wet compress is applied on a necrotic wound. A gauze is wound two turns around the compress in order to affix it. This bandage is then further affixed with an adhesive plaster. The compress is soaked every fourth hour with the composition. In order to limit the application only to that part of the compress which covers the wound, the mixture is applied by the use of an injection cannula having a coarse apex. Once a day, the whole dressing is removed and replaced by a fresh dressing. During this operation degraded and disintergrated necrotic parts must be removed mechanically. In the specific treatment carried out, the wound appeared clean after 1 week.

EXAMPLE 5

Effect of krill enzymes on necrotic materials

In order to examine the effect of the krill enzymes on necrotic components existing on the skin of humans, the following experiment was carried out:

Necrotic material was applied on the intact skin of the upper side of the right hands of two persons. The necrotic material was from a wound in a leg. The material consisted of devitalized collagen tissue, coagulated blood, fibrin, pus and crusts. The amount applied for each person was 0.5 g.

The necrotic material on each person was covered with a compress (area 10 cm$^2$), which has been soaked with the krill enzyme composition prepared as in example 4. Each compress was covered with a gauze. After 4 hours both of the compresses were nearly completely dry and therefore more of the enzyme composition had to be added. After 12 hours the compresses were removed and the necrotic material remaining on each hand was weighed separately. The material showed characteristic signs of degradation and had decreased their weights with about 25%. The skin, contacted with the necrotic material during the test, were unaffected. No negative symptoms were experienced by the test persons.

EXAMPLE 6

In vivo test on a person having a minor necrotic wound

A person having a minor ulcer containing necrotic material ion his right forefinger, treated himself over a period of 5 days with daily application of a 1% krill enzyme solution (prepared as in example 4). The wounded area tolerated the enzyme composition well and showed a significant tendency to become clean and to epithelialize. No adverse effects were observed.

EXAMPLE 7

The cleaning effect on lipid rich seborrhoic skin by krill enzymes combined with an amphoteric tenside A conventional detergent was used consisting of 18,00% (w/w) alkylimidazoline, 1,90% (w/w) laurylpolypeptid condensate, 1,70% (w/w) undecylenlypolypeptid condensate, 28,00% (w/w) modified alkyl ether sulfate buffered with fat substances (lanoline), 1,40% (w/w) coconut-amine sarcosinate, 1,90% (w/w) undecylene acid, 2,00% (w/w) undecylene-monoethanolamide sulfosuccinate, lactic acid q.s. pH 6,4 and aqua bi dest and 100,00% (w/w).

An amount of the lyophilized krill enzyme preparation (from example 1B) was added to the detergent giving a 1% (w/w) enzyme detergent composition. An area of 10 cm$^2$ of skin in regio sternalis of two persons, having an apparent seborrhoea oleosa in this region, was selected for testing. These areas were washed twice a day during five days with the enzyme detergent composition. Samples from the same area were taken both before and after the washing period. The samples were collected and analysed photometrically according to Schaeffer H and Kuhn-Bussius H. (Arch. Klin. u. exper. Dermatol. 238 (1970) p. 429).

The result showed a significant decrease in the transmission value for both of the two persons examined. Hence, this indicates a degradation of the lipid of the skin by the enzyme composition used. Comparatively very little effect was obtained, when the two persons used only detergent in the absence of enzymes.

EXAMPLE 8

Comparative washing experiments on textile. A comparison between enzyme from *E. superba* (krill), Alcalase ® and distilled water Equal pieces (5×5 cm) were cut from a homogenous part of a cloth. The cloth was twofolded having one side of silk and the other of a weft consisting of a mixture of cotton and synthetic fibers. Six of the pieces were stained with blood, six with milk and six with indian ink. To each of six Ehrlenmeyer flasks, 100 ml of an aqueous solution (0.5% w/v) of the lyophilized krill enzyme were added (the lyophilized krill enzyme was obtained from example 1B). To each of six other Ehrlenmeyer flasks, 100 ml of a 0.5% (w/v) of Alcalase ® (Novo Industri, Copenhagen, Denmark) solution in aq. dest were added. 100 ml aq. dest were added to six other Ehrlenmayer flasks.

To each of two flasks containing the kirll enzyme solution, to each of two flasks containing the Alcalase ® solution and to each of two flasks containing aq. dest, one of the pieces stained with blood was added. Analogously, the other stained pieces were added to the remaining flasks, so that only one piece was present in each flask. This meant that each of the compositions were allowed to act in duplicate on cloth stained with blood, milk and indian ink. Thereafter, the flasks were agitated on a shaking water bath for one hour at +45° C. After this treatment, the washing liquid was decanted and 100 ml aq. dest were added to each flasks. The flasks were then sealed with a rubber plug and agitated heavily for one minute. Thereafter the pieces of cloth were collected and washed slowly in flowing tap water for 10 minutes. The pieces were folded in clean white towels and allowed to dry.

The effect of the washing, i.e. the brightness of the cloth, was then determined by a double blind test, i.e. the examiner did not know which washing composition each piece had been treated with. The washing effect, i.e. the brightness and cleanness of the cloth, was evaluated visually in the order of precedence; 0=completely clean cloth; 1=insignificant amounts of remaining dirt; 2=moderate amount of remaining dirt; 3=considerable amounts of reamining dirt. The results from the washings are presented in Table 1.

TABLE 1

The washing effect of 0.5% (w/v) krill enzyme in aq. dest; 0.5% (w/v) Alcalase ® in aq. dest; and aq. dest without addition of enzymes.

| Contaminants | 0.5% krill-enzyme in aq. d. Cloth I | 0.5% krill-enzyme in aq. d. Cloth II | 0.5% Alcalase ® in aq. d. Cloth I | 0.5% Alcalase ® in aq. d. Cloth II | aq. dest alone Cloth I | aq. dest alone Cloth II |
|---|---|---|---|---|---|---|
| Blood | 1 | 1 | 2 | 2 | 2 | 3 |
| Milk | 1 | 1 | 2 | 1 | 2 | 2 |
| Indian ink | 2 | 2 | 2 | 2 | 3 | 3 |

From Table 1 it is seen that the enzyme composition from krill is more effective than Alcalase ® or aq. dest. Similar tests can be performed with an analogous composition containing capelin enzymes.

EXAMPLE 9

Degradation of fibrin, necroses and coagulated blood

A. Fibrin

Fibrin was dissected into pieces varying in weight from 0.2–0.3 g. For each enzyme composition used, 20 test tubes were numbered and to each of them one piece of preweighed fibrin was added. To the 20 tubes of each composition, equal amounts of the enzyme composition were added. Varidase ® was used in the dilution of 1:20 (w/v based on the commercial preparation) in destilled water. Trypure ® was used in the concentration of 1:15 (w/v based on the commercial preparation) in saline. The preparations of the other enzymes used were diluted in saline and the concentrations of the composition so obtained are given in Table 2. The krill enzymes and capelin enzymes used were the lyophilized preparations obtained according the example 1B and 2, respectively. The study was performed at a temperature of +33° C. which is the same as the temperature in wounds. After 12 hours and 24 hours, respectively, the reactions were stopped and the fibrin remaining was collected and kept on a wet filter paper for 60 seconds and weighed. Papain, Ficin and Pankreatin were all obtained from E. Merck, Darmstadt, Germany.

TABLE 2

The influence of different enzyme compositions on fibrin. Concentrations are given in % w/v.

| Enzyme | Reading after 12 hour | Reading after 24 hour |
|---|---|---|
| Trypure ® | ---- | nothing left |
| Varidase ® | -- | -- |
| Ficin 1% | - | - |
| Papain 1% | -- | -- |
| Pankreatin ® 1% | --- | --- |
| Krill enzymes 1% | ---- | nothing left |
| Capelin enzymes 1% | ---- | nothing left |

- denotes 0–25% decrease in weight
-- denotes 26–50% decrease in weight
--- denotes 51–75% decrease in weight
---- denotes 76–100% decrease in weight Fibrin was dissolved in the shortest time by the composition containing krill enzymes, capelin enzymes and Trypure ® and in the order given. Varidase ® and Alacalase ® were similar to ficin, and papain has the weakest effect.

B. Degradation of necroses

Necroses were dissected in pieces of 0.2–0.3 g. For each enzyme composition used, 20 test tubes were numbered and to each of these tubes one piece of the preweighed necroses were added. To the 20 test tubes of each composition, equal amounts of each enzyme composition were added. The compositions used are given in Table 3 and their concentrations are given as % (w/v) in saline. Varidase ® and Trypure ® were diluted according to example 8A. After time intervals of 12, 24, 36 and 72 hours, the degradation was stopped and the necroses were collected and weighed.

TABLE 3

The influence of different enzyme compositions on necroses. Concentrations in % are calculated on a w/v basis.

| Enzyme composition | Conc. | 12 hrs | 24 hrs | 36 hrs | 72 hrs |
|---|---|---|---|---|---|
| Varidase ® | 1:20 (w/v) | +++ | +++ | | |
| Trypure ® | 1:15 (w/v) | ++ | ++ | | |
| Ficin | 0.5% | 0 | 0 | 0 | — |
| | 1.0% | + | 0 | -- | --- |
| | 2.0% | + | — | — | -- |
| Papain | 0.5% | 0 | + | | + |
| | 1.0% | 0 | + | | + |
| | 2.0% | + | + | + | + |
| Alcalase ® | 0.5% | 0 | — | 0 | — |
| | 1.0% | — | — | -- | -- |
| | 2.0% | — | — | — | — |
| Krill enzymes | 0.5% | — | -- | -- | -- |
| | 1.0% | -- | --- | --- | --- |
| | 2.0% | — | --- | ---- | ---- |
| Capelin enzymes | 0.5% | -- | -- | --- | --- |
| | 2.0% | — | --- | --- | --- |
| Pankreatin ® | 0.5% | 0 | ++ | ++ | ++ |
| | 1.0% | + | +++ | +++ | +++ |
| | 2.0% | ++ | ++++ | +++ | +++ |

---- decrease in weight 76–100%
--- decrease in weight 51–75%
-- decrease in weight 26–50%
- decrease in weight 1–25%
0 status quo 0%
+ increase in weight 1–25%
++ increase in weight 25–50%
+++ increase in weight 51–75%
++++ increase in weight 75–100%

Apparently, Alcalase ®, krill enzymes and capelin enzymes are really able to dissolve necroses and do not increase the water content thereof like Varidase ®, Trypure ®, and saline. However, when regarding their influence on the necroses, papain and Pankreatin ® show the same tendencies as the compositions on the market, i.e. an increase in weight due to an increase in water content. Ficin has an effect similar to but weaker than Alcalase ®, the krill enzymes and the capelin enzymes.

C. Degradation of coagulated blood

Coagulated blood was dissected and portioned into test tubes arranged as in example 9A and B. The enzyme preparations used were dissolved in saline, and the concentrations (% w/v) of the compositions so obtained are given in Table 4. After the time intervals 12 and 24 hours, respectively, the degradation was stopped, and the blood coagels were collected and weighed.

TABLE 4

The influence of different enzyme compositions on coagulated blood.

| Enzyme composition | conc. | 12 hrs | 48 hrs |
|---|---|---|---|
| Varidase ® | 1:20 (w/v) | — | -- |
| Saline | 0.9% | — | — |
| Ficin | 1.0% | — | -- |
| Papain | 1.0% | — | — |
| Alcalase ® | 1% | — | — |
| Pankreatin ® | 1.0% | -- | -- |
| Krill enzymes | 1.0% | --- | ---- |

TABLE 4-continued

| The influence of different enzyme compositions on coagulated blood. | | |
|---|---|---|
| Enzyme composition | Reading after | |
| conc. | 12 hrs | 48 hrs |
| Capelin enzymes 1.0% | — | — |

— decrease in weight 0-25%
— — decrease in weight 26-50%
— — — decrease in weight 51-75%
— — — — decrease in weight 76-100%

From Table 4 it is seen that for coagulated blood, the krill enzymes were superior to the capelin enzymes, which both showed an effect superior to the other enzyme compositions investigated.

EXAMPLE 10

Studies of different enzyme compositions on healthy skin

Different solutions of ficin, papain. Alcalase ®, Pankreatin ®, krill enzymes and capelin enzymes—all at concentrations of 1% (w/v)—were applied (0.3 ml) on the healthy skin of two experimental persons and covered by a thin bandage. No sign of inflammation could be observed on the skin after 12 hours. The same observation was found when using Varidase ® and Trypure ®. Hence, the enzymes apparently only attack necrotic tissues in the concentration ranges used in the tests.

We claim:
1. In a process for the enzymatic debridement of living tissues by the application of an enzyme to the tissues being bebrided; wherein the improvement comprises the application of an enzymatic debriding effective amount of purified enzymes comprising a mixture of exo- and endopeptidases isolated from krill of the order Euphausiaceae.
2. A process according to claim 1 in which the enzymes isolated from krill of the order Euphausiaceae have molecular weights range of 15,000–80,000 dalton.
3. A process according to claim 1 in which the enzymes are isolated by a process which comprises homogenizing the krill and extracting the enzymes from the homogenized krill with an aqueous media.
4. In a process for the therapeutical cleaning of living tissue by the application of enzymes to the tissue be cleaned; wherein the improvement comprises the application of a therapeutically cleaning effective amount of purified enzymes comprising a mixture of exo- and endopeptidases isolated from krill of the order Euphausiaceae.
5. A process according to claim 4 in which the enzymes isolated from krill of the order Euphausiaceae have molecular weights in the range of 15,000–80,000 dalton.
6. A process according to claim 4 in which the enzymes are isolated by a process which comprises homogenizing the krill and extracting the enzymes from the homogenized krill with an aqueous media.

* * * * *